United States Patent [19]

Magee et al.

[11] 4,288,604
[45] Sep. 8, 1981

[54] METHOD FOR THE PRODUCTION OF TETRAALKYL SILICATES

[75] Inventors: Walter L. Magee, Danbury, Conn.; Jeffrey E. Telschow, Tarrytown, N.Y.

[73] Assignee: Stauffer Chemical Company, Westport, Conn.

[21] Appl. No.: 151,226

[22] Filed: May 19, 1980

[51] Int. Cl.$^3$ .............................. C07F 7/04; C07F 7/18
[52] U.S. Cl. ..................................................... 556/470
[58] Field of Search ......................................... 556/470

[56] References Cited

U.S. PATENT DOCUMENTS

| 3,627,807 | 12/1971 | Bleh et al. | 556/470 |
| 3,803,197 | 4/1974 | Anderson et al. | 556/470 UX |
| 4,113,761 | 12/1978 | Kreuzburg et al. | 556/470 |
| 4,197,252 | 4/1980 | Joch et al. | 556/470 |
| 4,211,717 | 7/1980 | Emblem et al. | 556/470 |

Primary Examiner—Paul F. Shaver
Attorney, Agent, or Firm—Henry Z. Friedlander

[57] ABSTRACT

Tetraalkyl silicates are produced by the reaction of silicon metal with an alkanol in the presence of an alkali metal salt of an alkoxyalkoxy alcohol or a polyalkylene glycol in either an alkoxyalkoxy alcohol or a polyalkylene glycol or mixtures thereof and recovery of the product. Tetramethyl silicate and tetraethyl silicate are the preferred products. The preferred alkoxyalkoxy alcohol is 2-(2-butoxyethoxy)ethanol. The preferred glycol is diethylene glycol. An indifferent solvent and/or a hydroxide-scavenger may be employed in the reaction mixture.

23 Claims, No Drawings

METHOD FOR THE PRODUCTION OF TETRAALKYL SILICATES

BACKGROUND OF THE INVENTION

1. Field of the Invention

This invention relates to the production of tetraalkyl silicates, particularly tetraethyl and tetramethyl silicates.

Alkyl silicates can be made by the first reaction of metallic silicon with the corresponding alkanol. This route requires either high temperature, high pressure, high surface area of the metal, or a combination of these to achieve a practical reaction rate.

Silicon halides can be caused to react with alkanols to make organosilicates. The process produces large amounts of hydrogen chloride which is corrosive and presents a disposal problem.

Electrolytic methods may be employed to produce tetraalkyl silicates. The electrolytic process requires a large capital expenditure, has high operating expenses, and may involve difficult problems of separation.

Another route to tetraalkyl silicates involves transesterification, wherein a high-boiling alcohol reacts with silicon to form an intermediate silicate which then reacts with a lower boiling alkanol to form the desired tetraalkyl silicate.

2. Description of the Prior Art

Anderson et al in U.S. Pat. No. 3,803,197 granted Apr. 9, 1974 disclose a process for preparing alkyl and 2-alkoxyethyl orthosilicates by reacting "simple alcohols" or 2-alkoxyethyl alcohols containing 1–4 carbon atoms in the alkoxy group with silicon in the presence of a catalytic amount of an alkali metal salt of a 2-alkoxyethyl alcohol. This patent teaches preparation of a catalytic alkali metal alkoxide from the metal. Anderson et al apply their invention to both the synthesis of higher boiling orthosilicates and lower boiling silicates.

The preparation of tetraethyl orthosilicates from a source of silicon suspended in tetraethyl silicate and ethanol, catalyzed by a large amount of sodium ethoxide and cocatalyzed by either an ether alcohol or an alkanolamine, is described by Flick et al in British patent application No. 2,018,800A published Oct. 24, 1979 (cf. West German patent application No. 2,816,386 published Oct. 25, 1979).

A process for synthesizing tetraalkyl orthosilicates by contacting a source of silicon with an alcohol and its corresponding alcoholate is the subject of U.S. Pat. No. 4,113,761 granted Sept. 12, 1979. The process of this disclosure requires additionally either a surface active agent, sodium methylate, or the use of pressure (cf. British patent applications No. 1,559,335-6-7).

Bleh et al in U.S. Pat. No. 3,627,807 granted Dec. 14, 1971 disclose a method for preparing tetraalkyl silicates from an alcohol and the corresponding alcoholate in the presence of a large amount of the same tetraalkyl silicate ester. The patent discloses stringent limitations on the ratios of the materials in the reaction mixture and all three compounds (the alcohol, the alcoholate, and the ester) are restricted to the same alkyl group.

U.S. Pat. No. 2,927,937 granted Mar. 8, 1960 to Gaines sets forth a method for preparing alkyl orthosilicates by attrition milling of a silicon source in the presence of an alcohol and an alkaline catalyst, preferably under pressure. One of the five preferred catalysts disclosed by Gaines is sodium ethoxide. Extended ball milling is required for this process.

3. Objects of the Invention

A principal object of this invention is to provide a method for preparing tetraalkyl silicates.

Another object of this invention is to lessen the formation of by-products, especially unsymmetrical mixed esters, in the preparation of tetraalkyl silicates.

Still another object of this invention is to provide a safe and convenient method for preparing potassium alkoxides and potassium glyoxides suitable as catalysts for the reaction of silicon metal and alkanols to make tetraalkyl silicates.

Another object of this invention is to provide a clean surface of silicon at all times during the reaction.

A further object of this invention is to provide a process for the preparation of tetraalkyl silicates which is amenable to continuous operation.

Other objects of this invention will be apparent to the reader from the description and examples below.

SUMMARY OF THE INVENTION

Tetraalkyl orthosilicates are produced from the combination of silicon with a low-boiling alkanol in a reacting mixture of a high-boiling alkoxyalkoxy alcohol or alkylene glycol and an alkali metal salt of the alcohol or glycol. The alkali metal salt is prepared by reaction of the high-boiling alcohol or glycol with an alkali metal hydroxide preferably potassium hydroxide. The alkali metal glycolate or alkoxyalkoxy alkoxide, preferably dissolved in the corresponding alcohol or glycol, catalyses reaction with a source of silicon metal thus generating hydrogen. Then, after the initial production of hydrogen, an alkanol, such as methanol or ethanol, is added to the reaction mixture to produce the tetraalkyl silicate.

During the process of this invention five different silicate esters can be present in the reaction mixture. The possible silicate esters can be designated AAAA, AAAB, AABB, ABBB, and BBBB where A represents the alkoxyalkoxy or glycolic moiety and B represents the methoxy or ethoxy moiety. In the case of tetraethyl silicate (BBBB) and tetra 2-(2-butoxyethoxy)ethyl silicate (AAAA), for example, one utilizes the difference in boiling point between the desired product, BBBB, and its closest-boiling contaminant, ABBB. The instant invention provides a process in which the silicate product is readily separated from the reaction mixture.

The process of this invention is easily adaptable to continuous operation. An indifferent solvent and/or a hydroxide-scavenger may be employed.

DESCRIPTION OF THE INVENTION

The instant invention is an improvement in the process for the preparation of tetraalkyl silicates from silicon metal or its alloys. The process involves the reaction of an alkanol in a mixture of a source of silicon metal, a high boiling alcohol or polyalkylene glycol, and an alkali metal salt of the high boiling hydroxy compound. Additionally, an indifferent solvent, such as toluene, is optional; a hydroxide-scavenger is preferred. The reacting mixture is believed to contain the following silicate ester compositions; the exact composition of the reacting mixture is however unknown. Therefore, the following equation is set forth merely as an aid in explaining the advantages of the present invention:

$(R'O)_4Si \rightleftharpoons (R'O)_3SiOR \rightleftharpoons (R'O)_2Si(OR)_2 \rightleftharpoons R'OSi(OR)_3 \rightleftharpoons (RO)_4Si,$ where R of the low-boiling alkanol and R' of the high-boiling hydroxy compound are described immediately below.

The desired product of the process is represented by $(RO)_4Si$, where R is derived from an aliphatic alkanol containing one to six carbon atoms, either normal, branched, or alicyclic; preferably ethyl, methyl, propyl, or isopropyl.

The high-boiling hydroxy compound may be an oligomeric alkylenic glycol or the monoalkyl ether of such a glycol. Alkoxyalkoxy alcohols are the preferred type, among which 2-(2-butoxyethoxy)ethanol, trade name Butyl Carbitol, is especially preferred. Among the glycols, diethylene glycol is preferred. The boiling point of the high-boiling alcohol should be higher than that of the desired tetraalkyl orthosilicate being prepared. In the equation above the non-hydroxy moiety of the high boiling hydroxy compound is represented by R'. The high-boiling hydroxy compounds for forming the intermediate $(R'O)_4Si$ preferably are commercially available and reasonable in price. Unexpectedly, alkoxides or glyoxides of higher molecular weight are in fact easier to synthesize from the metal hydroxides and thus have greater utility for a practical process than those of a lower molecular weight. Glycols of shorter chain length may also form cyclic silicates and hence are less desirable as high boiling hydroxy compounds than those of the present invention.

Compounds represented by the formula:

$$R''O(CHR'''CH_2O)_nH$$

where R'' is selected from the group consisting of hydrogen, ethyl, butyl, methyl, propyl, hexyl, cyclohesyl, 2-ethylhexyl, their isomers and mixtures; R''' is either hydrogen or methyl; and n is equal to 2, 3, or 4 are useful in the practice of this invention.

Normally in the present invention the catalytic alkaline metal salt is derived from the same moiety as the high-boiling hydroxy compound employed, but another alkoxide can be used as the source of catalyst. Preferably, the alcohol from which the alkoxide is prepared has a boiling point at least equal to that of the alcohol R'OH.

The salt is preferably that of an alkali metal such as lithium, sodium, potassium, rubidium, or cesium. Sodium and potassium are preferred for economic reasons, while potassium is most preferred because its salts in solution have a lower viscosity than the alkoxides of other alkali metals. It should be emphasized that is is preferably to make the potassium alcoholate from potassium hydroxide rather than potassium metal. Using the hydroxide rather than the metal is cheaper, easier, safer for the plant operators, and obviates the pyrophoric properties of alkali metals.

It is critical to scavenge any residual hydroxide from the reaction mixture before contacting the silicon or silicon source with the catalyst solution, because any residual hydroxide can cause coating of the surface of the silicon with an insoluble material resulting in an unreproducible rate of reaction. Previous workers, mentioned in the Prior Art section, employed elemental alkali metal to prepare the alcoholate. Since nowhere do they disclose drying their reagents, any advantitious water would produce alkali metal hydroxides which cause the effects mentioned above. On a commercial scale use of alkali metal hydroxide as the source of alkali metal atoms is highly preferred. Any water present can attack the catalyst regenerating hydroxide:

$$R'OM + H_2O \rightleftharpoons R'OH + MOH$$

where M is an alkali metal.

Hydroxide-scavengers are compositions which remove strong alkali irreversibly from the reaction mixture to form low-strength bases. This enables the silicon surface to remain clean and etched with its crystalline domains clearly defined.

Hydroxide-scavengers in transforming a strong base to a weaker base are useful in improving the reproducibility of processes which produce tetraalkyl orthosilicates by reaction of silicon with an alkanol catalyzed by an alkali metal alkoxide. The processes described by Anderson in U.S. Pat. No. 3,803,197 and Kreuzburg et al in U.S. Pat. No. 4,113,761 are presentative of those improvable by use of a hydroxide-scavenger.

Carbon dioxide is an excellent hydroxide-scavenger as is dimethyl or diethyl carbonate and other carboxylic esters. Tetraalkyl orthosilicates are also preferred hydroxide scavengers, especially tetramethyl or tetraethyl orthosilicates, making it advantageous to commence the reaction in the presence of some product.

The source and nature of the silicon metal greatly influences the ease, speed, and yield based on silicon in the preparation of tetraalkyl orthosilicates. Generally metallurgical-grade silicon, alloys such as ferrosilicon of the 10/90 composition, or silicides are the practical sources of choice. For continuous operation, metallic silicon is preferably to ferrosilicon, silicon bronze, silicon copper, or silicon zirconium because there is then no appreciable build up to extraneous metal in the reaction zone. Depending on pricing, however, silicon alloys may have an economic advantage for the amount of silicon reacted.

The greater the surface area of the silicon metal the faster the rate of reaction. Therefore, powdered silicon or silicon alloys are preferable to the commercially available lump silicon metal. Particles smaller than 50 micrometers (mircons) are advantageous. For optimum reactivity silicon particles 20 microns or less in diameter are preferred. Silicon or its alloys, wherein more than 80 percent of the particles are less than 20 microns in diameter, can be obtained by hammer milling lump, commercial material and then reducing the particle size of the coarse product to finely comminuted particles in a jet mill. Cryogenic milling under liquid nitrogen may be employed.

A broad temperature range may be employed for synthesis of the silicates from silicon. At atmospheric pressure a temperature range of from about 2° to about 60° C. above the boiling point of the desired orthosilicate is used. Tetramethyl silicate is generally prepared at a temperature in the range of about 125°–190° C. Tetraethyl silicate is generally prepared in the range of about 170°–240° C. Since the synthesis can be carried out under either reduced or elevated pressure, the temperature ranges stated above denote only atmospheric conditions. At atmospheric pressure for the synthesis of tetraethyl orthosilicate (b.p. about 168° C.) the preferred temperature is from about 170° to about 220° C. For the preparation of tetramethyl silicate (b.p. about 121° C.), the preferred temperature range is from about 125° to about 155° C.

It is preferably to add the low-boiling alkanol to the powdered silicon metal when it is in contact with the alkoxyalkoxy alkoxide or glyoxide salt solution. The molar ratio of alkanol to silicon may vary from about two to about eight. If a continuous operation is desired, metallic silicon or alloy also is added continuously during the reaction. Low-boiling alkanol is also added during the operation so that the alkanol/silicon molar ratio remains at a value below about four.

A clean silicon surface, whether from metal or alloy, leads to a short induction period for the reaction. When potassium 2-(2-butoxyethoxy)ethoxide is the catalyst and clean metal is used, the induction period can be eliminated, especially in the presence of a hydroxide-scavenger. When the initial charge of silicon is introduced into the reaction, evolution of hydrogen occurs. It is generally preferred to add the low-boiling alkanol (ROH) after the evolution of hydrogen has subsided. Overall the following reactions are believed to be taking place simultaneously, wherein R'OH is the high-boiling alkoxyalkoxy alcohol or glycol:

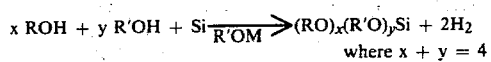

where x + y = 4

Whether the alkali metal alkoxide or glyoxide is made separately or in situ it is advantageous to remove the water formed or introduced before adding silicon or a source of silicon to the reaction mixture. This is conveniently done by azeotropic distillation, for which toluene is the preferred boiling agent.

In carrying out the process of this invention, the desired tetraalkyl orthosilicate can be distilled from the reaction vesel as it is formed. This is shown by the vertical arrow at the end of the second equation immediately above. At the same time, however, some of the low-boiling alkanol, ROH, is also removed from the reacting mixture since it has a lower boiling point than the tetraalkyl silicate. One then has the option of continuously fractionating the product with alkanol recycle. Or, one can purify the tetraalkyl silicate separately, as described in Example 4.

Tetraalkyl silicates have great utility in the coating of metals, as ceramic binders, or for precision casting (the "lost wax" process).

In the preparation of tetraethyl silicate (b.p. 168° C.) the highest boiling intermediate alcohol previously used, 2-butoxyethanol (b.p. 171° C.), shows only a small temperature gap of three degrees. The preferred alcohol for practicing the instant invention, 2-(2-butoxyethoxy)ethanol (b.p. 231° C.) provides a temperature difference of 60 degrees, enabling one to purify the tetraalkyl silicate much easier.

The following examples illustrate certain embodiments of this invention, but should not be interpreted as limiting the scope of protection which is sought.

COMPARATIVE EXAMPLE 1

The data below emphasize gas chromatographic retention times as a measure of separability, rather than boiling points, because precise measurements of retention time can be quickly made on a small amount of pure material. The advantage of using an alkoxy-alkoxy ethanol or an alkylenic glycol lies in the greater difference in boiling point between the desired tetraalkyl silicates and the potentially interfering mixed esters.

A gas chromatograph (Hewlett Packard Model 5750) was fitted with a two-meter column, 0.31 cm in diameter, containing a packing of 100/120 Supelcoport coated with a silicone oil (SP 2250 from Supelco of Bellefontaine, Penna.). The chromatographic column was operated at 200° C. The retention times were measured for the series of compounds by injecting one microliter of a mixture of these materials and comparing their retention in the above column with the known components.

| Compound | Retention Time (in minutes) |
|---|---|
| ethanol | 0.23 |
| tetraethyl silicate | 0.49 |
| butoxyethanol | 0.77 |
| butoxyethoxyethanol | 1.24 |
| butoxyethyl triethyl silicate | 2.87 |
| butoxyethoxyethyl triethyl silicate | 4.52 |
| dibutoxyethyl diethyl silicate | 6.0 |
| dibutoxyethoxyethyl diethyl silicate | more than 10.0 |

The larger difference in retention times between tetraethyl silicate and butoxyethoxyethanol or butoxy ethoxyethyl triethyl silicate compared to that between tetraethyl silicate and butoxyethanol or butoxyethyl triethyl silicate indicate that separation of the reaction product from potential contaminants is made easier by the process of the instant invention.

The boiling points of some of the compounds used in the instant invention are given below to illustrate its potential utility:

| Compound | Boiling Point °C. |
|---|---|
| methanol | 64.7 |
| ethanol | 78.4 |
| tetramethyl orthosilicate | 120.8 |
| tetraethyl orthosilicate | 165.5 |
| ethoxyethanol | 135° |
| butoxyethanol | 171° |
| ethoxyethoxyethanol | 208° |
| butoxyethoxyethanol | 231° |
| diethylene glycol | 245° |
| triethylene glycol | 278° |
| tetraethylene glycol | 327° with decomp. |

EXAMPLE 2

Example 2 illustrates the preparation of a potassium alkoxide salt used in the practice of the instant invention.

Into a one-liter, round-bottom flask equipped with a magnetic stirring bar, thermometer, gas inlet, Dean-Stark trap, and heating mantle were placed 2.0 moles (324.4 g) of 2-(2-butoxyethoxy) ethanol, 50 ml of toluene, and 1.0 mole (65.4 g) of pelletized potassium hydroxide. A nitrogen gas line was attached, and the trap was filled with toluene (about 25 ml) before heating was commenced. After about 2.5 hours of heating at reflux with strong agitation under nitrogen, 24 ml of water had been azeotropically removed. At this point the trap was replaced by a distilling head, and 75 ml of toluene distilled off at about 120° C. The resulting yellow solution was cooled and stored under nitrogen.

Upon titration of an aliquot of the yellow solution of alkoxide in alcohol with 0.1 N HCl to the p-napthol benzoin end point (green), the strength of potassium alkoxide was shown to be 2.55 mmol/g solution.

EXAMPLE 3

Example 3 illustrates the preparation of tetraethyl orthosilicate by the method of this invention.

A 250-ml, three-neck, round bottom flask was equipped with a rubber septum, a mechanical stirrer with Teflon blade, a separable distilling head, and a 500-ml receiver with thermometer. Under nitrogen, 1 mole (28 g) of 96% silicon metal dust, previously milled and reduced to about 20-micron diameter in a Trost jet mill, was charged to the flask, followed by 50 g of the potassium 2-(2-butoxyethoxy) ethoxide in 2-(2-butoxyethoxy) ethanol prepared in Example 2. The flask was closed with the rubber septum, and nitrogen flow maintained on a bypass basis. The flask was heated to 180° C. with stirring at 150 rpm, and the nitrogen line replaced by a wet test meter to measure the hydrogen produced. The evolution of hydrogen ceased after 2.5 l had been measured, whereupon dry ethanol was added beneath the surface of the liquid with a 16-gauge needle at 1.4 ml/min by means of a syringe pump. The addition of ethanol recommenced the generation of hydrogen. The temperature was maintained between 175° and 190° C. as the exothermic reaction proceeded. The amount of hydrogen generated was continuously measured by the wet test meter. Low boiling materials were continuously distilled from the reaction mixture. After 36–40 l of hydrogen had been produced and the rate of hydrogen formation was down to 5 l/hr, the addition of ethanol was stopped. At this point about 260 g of ethanol had been added to the three-neck flask.

The addition of silicon and ethanol was repeated twice more, whereupon 3 moles (84 g) of silicon had been treated with 795 g (17.3 moles) of ethanol to produce 508 g of crude tetraethyl silicate and a total of 10.4 g of hydrogen gas.

EXAMPLE 4

This example illustrates the redistillation of crude tetraethyl orthosilicate to purify it.

The product of Example 3 comprised tetraethyl orthosilicate containing some ethanol. A stirring bar was placed in the receiving flask from Example 3 and the flask fitted with a 13-cm Vigreux column and a distilling head. After distilling off the ethanol, a mixture weighing 480 grams remained containing 96% tetraethyl orthosilicate by gas chromatographic analysis.

EXAMPLE 5

This example illustrates the use of a small-volume run to produce catalyst for the initial charge of a larger volume continuous run, described in Example 6.

A 500-ml, round-bottom flask was equipped with a heater, stirrer, pot thermometer, insulated take-off head, take-off thermometer, nitrogen inlet, nitrogen purge water, receiving vessel, and wet test-meter to measure the hydrogen gas evolved.

The flask was charged initially with 200 g of a 50 percent solution of the potassium salt of 2-(2-butoxyethoxy) ethanol dissolved in that alcohol, prepared as in Example 2. The nitrogen purge was started at about 3 l/hr, the stirrer run at about 350 rpm, heating commenced, and after 10 minutes of purge, 56 g of milled elemental silicon powder (97 percent pure) with an average particle size of about 60 microns was added all at once. At a pot temperature of 150° C. the nitrogen purge was turned off. In the range of about 175° to 190° C. hydrogen gas evolved in a variable fashion peaking at a rate of about 6 l/hr. The pot was held in the 185°–190° C. range during the evolution of hydrogen, which continued for several hours. When the rate of hydrogen evolution had diminished to about 0.5 l/hr, ethanol (2B grade) was introduced at a rate of about 36 g/hr. The addition of ethanol continued for several hours.

Optionally, in order to produce more intermediate silicate esters, on the second day the process of the preceding paragraph may be repeated with an additional charge of catalyst solution and an additional charge of milled silicon powder. The copious evolution of hydrogen signals the reaction of silicon metal, producing the intermediary high-boiling alkoxyalkoxy orthosilicates.

Upon preparation of the intermediates, maintaining a reaction temperature of about 180°–200° C., and introduction of ethanol, vapor was taken off at a rate of about 38 g/hr and condensed. The condensate comprised a crude mixture of 53% tetraethyl silicate and 47% ethanol. This reaction can be sustained continuously, as long as silicon and ethanol are added to the reactor and the crude product distilled off and condensed.

As in Example 4, the crude condensate was distilled to remove the ethanol and produce tetraethyl orthosilicate of purity about 98.8 to 99.2 percent.

EXAMPLE 6

This Example illustrates use of a three-liter reactor, charged initially with catalyst solution, to produce tetraethyl silicate intermittently for over 200 hours of reaction time.

A three-liter cylindrical reactor in vertical orientation about 40 cm high and about 10 cm in diameter bearing three internal baffles extending 1.5 cm inward was equipped with a stirrer, a source of nitrogen gas, a take-off head, a pot thermometer, take-off thermometer, a receiving vessel, and a wet test meter to measure the amount of hydrogen evolved.

Initially the reactor was charged with 410 ml of reaction mixture produced as in Example 5, supplemented by 235 ml of 50 percent potassium salt of 2-(2-butoxyethoxy) ethanol dissolved in that high-boiling alcohol as fresh catalyst and about 100 g of suspended silicon powder milled to a size of about 50 microns. The nitrogen purge started at a rate of about 3 l/hr; the stirrer was started at about 350 rpm, and the heating was begun.

The reaction was run at about 195° C. with the following typical parameters; silicon powder charge rate about 15 g/hr; ethanol addition (2B grade) about 138 g/hr; hydrogen production rate about 26 l/hr; tetraethyl silicate produced, about 94 g/h. This reaction was run for one shift per day over 28 working days for a total of 205 hours. The total recycled ethanol conversion efficiency was 95 percent; the one-pass ethanol efficiency 53 percent the overall silicon efficiency 73 percent. Overall 16.2 kg of tetraethyl orthosilicate was produced at 98 percent purity.

EXAMPLE 7

This Example illustrates the synthesis of tetraethyl silicate by the use of a catalyst prepared from the reaction of diethylene glycol with potassium hydroxide.

A 500-ml, three-necked, round-bottom flask was equipped with an oil bath, a mechanical stirrer, a pot thermometer, an addition funnel, a gas burette, and an insulated Claisen head fitted with a thermometer, leading to a distillation apparatus.

The reactor was charged with 100 g ethylene glycol dimethyl ether as solvent, 13.3 g (0.13 mole) diethylene glycol, and 7.0 g (0.12 mole) potassium hydroxide and heated within 20 minutes to 180° C. During the rise in temperature distillate (water) was collected for about six minutes. Then 14 g (0.5 mole) of cryogenically milled silicon was added in one portion to the catalyst solution, whereupon hydrogen gas began to evolve. At this point the dropwise addition of ethanol was commenced for an hour, while hydrogen continued to evolve.

Distillate was collected and analyzed by gas chromatography at 100° C. employing as the stationary phase 10 percent silicone oil (SE-30) in a 3-mm diameter column 2-m long. According to this analysis the distillate consisted of 13 percent tetraethyl silicate product, 42 percent ethanol which can be recycled along with 45 percent solvent, the dimethyl ether of ethylene glycol.

EXAMPLE 8

In the same manner as in Example 7, the catalyst was prepared by reaction of triethylene glycol with potassium hydroxide. As in Example 7, upon the addition of ethanol and silicon metal, tetraethyl silicate was prepared.

EXAMPLE 9

This example illustrates the rate of initiation and rate of reaction without the use of a hydroxide-scavenger.

A 250-ml flask, equipped as in Example 3, was charged with 120 g (0.33 mol) of a solution of the potassium salt of 2-(2-butoxyethoxy)ethanol in that alcohol, prepared as in Example 2, and 42 g (1.5 mol) of powdered silicon metal with the following size analysis: +200 mesh, 3 percent, 200-325 mesh, 26 percent, -325 mesh, 70 percent. This mixture was heated with stirring to 180° C. to effect an initial reaction of silicon with the high boiling alcohol accompanied by the evolution of hydrogen. After several hours the rate of hydrogen evolution had fallen from an early maximum of 43 ml/min to 10 ml/min, whereupon a stream of nitrogen was passed through the system at about 10 ml/min. The grade 2B ethanol was added to the reaction flask at a rate of 0.5 ml/min. The rate of hydrogen evolved averaged about 18 ml/min (maximum 26 ml/min) as 6.2 l was measured during the course of the reaction.

EXAMPLE 10

This example illustrates the effect on the rate of reaction by employing tetraethyl orthosilicate as a hydroxide-scavenger.

The procedure of Example 9 was followed except that before the powdered silicon was added to the reaction mixture 2.5 ml (11 mmol) of tetraethyl orthosilicate was stirred in. In this case the initiation was exothermic, a maximum rate of the evolution of hydrogen of 1 l/min was achieved. When this rate at 180° C. had fallen to 6 ml/min, the addition of 2B ethanol was begun. Hydrogen evolution averaged 71 ml/min (maximum 266 ml/min) as 31 liters of hydrogen was measured.

EXAMPLE 11

This Example illustrates the effect on the rate of reaction by employing carbon dioxide as a hydroxide-scavenger.

The procedure of Example 9 was followed except that before the powdered silicon was added to the reaction mixture 105 ml (7.1 mmol) of carbon dioxide gas was bubbled in from a lecture bottle at the rate of 7 ml/min. In this case the initiation was extremely exothermic causing a rise in temperature from 180° C. to 207° C. A maximum rate of the evolution of hydrogen of 2.6 l/min was achieved. When this rate at 180° C. had fallen to 2 ml/min, the addition of grade 2B ethanol was begun causing exothermic bursts of reaction. When the reaction had stabilized the rate of hydrogen evolution averaged 92.5 ml/min (maximum 300) as 17.1 liters of hydrogen was measured.

The effect of hydroxide-scavengers on the rate of reaction is summarized in Table I, based on the data of Examples 9, 10 and 11.

TABLE I

The Effect of Hydroxide-Scavengers

| Example | Scavenger | Initiation Rate Hydrogen Evolution (ml/min) | | Reaction Rate Hydrogen Evolution (ml/min) | |
|---|---|---|---|---|---|
| | | Average | Maximum | Average | Maximum |
| 9 | none | 24.4 | 43 | 18 | 26 |
| 10 | tetraethyl silicate | 74 | 1000 | 71 | 266 |
| 11 | carbon dioxide | 192 | 2600 | 92.5* | 300 |

*after stabilization

COMPARATIVE EXAMPLE 12

This Example illustrates the use of alkoxide ion of the prior art made, however, by reaction with potassium hydroxide, as in the instant invention, rather than by reaction with an alkali metal as practiced previously.

Into a single-necked, one-liter flask connected to a Dean-Stark trap phase separator and a condenser were charged 236 g. (2 moles) 2-butoxyethanol, 56 g (1 mole) potassium hydroxide, and 50 ml toluene solvent. The mixture was heated to reflux and 24 g water distilled off. Then 50 g of the resulting catalyst solution was mixed with 28 g (1 mole) silicon powder cryogenically milled to pass −200 mesh and 25 g (0.07 mole) tetraethoxyethyl silicate solvent and heated to 190° C. in a 250-ml, three-necked, roundbottom flask fitted with an oil bath, a mechanical stirrer, addition funnel and distillation head with condenser. When ethanol was added, vapors began distilling from the flask. After condensation, the distillate was analyzed by gas chromatography, which confirmed the presence of tetraethyl orthosilicate. After four moles of ethanol had been passed through the reactor, the residue was filtered to remove 9.2 g of unreacted silicon. Upon distillation and analysis of the volatile fractions, 98 percent pure tetraethyl silicate was isolated in 34 percent yield based on silicon.

The foregoing examples illustrate the instant invention. The scope of legal protection sought for this invention is set forth in the claims which follow.

We claim:

1. A process for the production of tetraalkyl orthosilicates which comprises reacting a source of silicon metal with an alkanol having 1 to 6 carbon atoms in the presence of an alkali metal salt of a high-boiling alcohol selected from the group consisting of compounds of the formula $R''O(CHR'''CH_2O)_nH$ where $R''$ is hydrogen, ethyl, butyl, methyl, propyl, hexyl, cyclohexyl, or 2-ethylhexyl, $R'''$ is hydrogen or methyl, n is equal to 2, 3, or 4, their isomers or mixtures thereof.

2. The process of claim 1 wherein the reaction is carried out in the presence of a high-boiling alcohol selected from the group consisting of compounds of the formula R"O(CHR"'CH$_2$O)$_n$H where R" is hydrogen, ethyl, butyl, methyl, propyl, hexyl, cyclohexyl, or 2-ethylhexyl, R"' is hydrogen or methyl, n is equal to 2, 3, or 4, their isomers or mixtures thereof.

3. The process of claim 1 wherein the alkali metal salt is a potassium salt prepared from potassium hydroxide and a high-boiling alcohol selected from the group consisting of compounds of the formula R"O(CHR"'CH$_2$O)$_n$H where R" is hydrogen, ethyl, butyl, methyl, propyl, hexyl, cyclohexyl, or 2-ethylhexyl, R"' is hydrogen or methyl, n is equal to 2, 3, or 4, their isomers or mixtures thereof.

4. The process of claim 1 wherein there are 2 to 4 moles of alkanol for each mole of silicon.

5. The process of claim 1 wherein the alkanol is ethyl alcohol.

6. The process of claim 1 wherein the alkanol is methyl alcohol.

7. The process of claim 1 wherein the high-boiling alcohol has the formula R""OCH$_2$CH$_2$OCH$_2$CH$_2$OH and R"" is selected from the group consisting of ethyl, butyl, cyclohexyl, hexyl, and 2-ethylhexyl moieties.

8. The process of claim 1 wherein the high-boiling alcohol is 2-(2-butoxyethoxy)ethanol.

9. The process of claim 1 wherein the alkali metal salt is selected from the group consisting of potassium, sodium, or lithium salts.

10. The process of claim 1 wherein the alkali metal is potassium.

11. The process of claim 1 which includes the additional step of separating the product from the reaction mass.

12. The process of claim 11 wherein the separation is carried out by distillation.

13. The process of claim 1 wherein the source of silicon metal is a powder about 70 or more percent of which comprises particles less than 50 micrometers in diameter.

14. The process of claim 1 wherein the high-boiling alcohol is triethylene glycol.

15. The process of claim 1 wherein the high-boiling alcohol is diethylene glycol.

16. The process of claim 1 wherein the process is carried out continuously.

17. The process of claim 2 wherein the process is carried out continuously.

18. The process of claim 2 wherein the process is carried out in the presence of an indifferent solvent.

19. The process of claim 2 wherein the process is carried out employing a hydroxide-scavenger.

20. The process of claim 19 wherein the hydroxide-scavenger is added to the alkali metal salt solution before addition of the source of silicon metal.

21. The process of claim 19 wherein the hydroxide-scavenger is selected from the group consisting of carbon dioxide, tetraethyl orthosilicate, tetramethyl orthosilicate, diethyl carbonate, and dimethyl carbonate.

22. In a process for the production of tetraalkyl orthosilicates by reacting a source of silicon metal with an alkanol having 1 to 6 carbon atoms in the presence of an alkali metal salt of an alcohol the improvement which comprises employing a hydroxide-scavenger.

23. The process of claim 22 wherein the hydroxide-scavenger is added to the alkali metal salt solution before addition of the source of silicon metal.

* * * * *

UNITED STATES PATENT AND TRADEMARK OFFICE
CERTIFICATE OF CORRECTION

PATENT NO. : 4,288,604
DATED : September 8, 1981
INVENTOR(S) : Walter L. Magee et al.

It is certified that error appears in the above—identified patent and that said Letters Patent is hereby corrected as shown below:

Col. 1, line 11, change "first" to -- direct --;

Col. 1, line 52, change "1979" to -- 1978 --;

Col. 4, line 19, change "presentative" to -- representative --;

Col. 4, line 36, change "up to" to -- up of --;

Col. 7, line 58, change "water" to -- meter --;

Col. 8, line 55, change "g/h." to -- g/hr. --;

Col. 10, line 49, change "distillatewas" to -- distillate was --.

Signed and Sealed this

Fifth Day of January 1982

[SEAL]

Attest:

Attesting Officer

GERALD J. MOSSINGHOFF
Commissioner of Patents and Trademarks